(12) United States Patent
Watson et al.

(10) Patent No.: US 8,827,917 B2
(45) Date of Patent: Sep. 9, 2014

(54) SYSTEMS AND METHODS FOR ARTIFACT DETECTION IN SIGNALS

(75) Inventors: James Watson, Dunfermline (GB); Paul Stanley Addison, Edinburgh (GB)

(73) Assignee: Nelleor Puritan Bennett Ireland, Galway (IE)

(*) Notice: Subject to any disclaimer, the term of this patent is extended or adjusted under 35 U.S.C. 154(b) by 1483 days.

(21) Appl. No.: 12/245,336

(22) Filed: Oct. 3, 2008

(65) Prior Publication Data
US 2009/0326871 A1 Dec. 31, 2009

Related U.S. Application Data

(60) Provisional application No. 61/076,934, filed on Jun. 30, 2008, provisional application No. 61/077,130, filed on Jun. 30, 2008.

(51) Int. Cl.
| | | |
|---|---|---|
| A61B 5/02 | (2006.01) | |
| G06F 19/00 | (2011.01) | |
| G06F 15/00 | (2006.01) | |
| G11C 17/00 | (2006.01) | |
| A61B 5/00 | (2006.01) | |
| A61B 5/04 | (2006.01) | |
| A61B 5/1455 | (2006.01) | |
| G06K 9/00 | (2006.01) | |

(52) U.S. Cl.
CPC .......... *A61B 5/14551* (2013.01); *A61B 5/7207* (2013.01); *A61B 5/04012* (2013.01); *G06K 9/00516* (2013.01); *A61B 5/726* (2013.01)
USPC .................... 600/502; 702/19; 700/1; 365/94

(58) Field of Classification Search
None
See application file for complete search history.

(56) References Cited

U.S. PATENT DOCUMENTS

| | | |
|---|---|---|
| 4,289,141 A | 9/1981 | Cormier |
| 5,285,783 A | 2/1994 | Secker |
| 5,291,884 A | 3/1994 | Heinemann et al. |
| 5,431,170 A | 7/1995 | Mathews |
| 5,439,483 A | 8/1995 | Duong-Van |
| 5,590,650 A | 1/1997 | Genova |
| 5,632,272 A | 5/1997 | Diab et al. |
| 5,778,881 A | 7/1998 | Sun et al. |
| 5,795,304 A | 8/1998 | Sun et al. |
| 5,797,840 A | 8/1998 | Akselrod et al. |
| 5,827,195 A | 10/1998 | Lander |
| 5,916,154 A | 6/1999 | Hobbs et al. |
| 5,967,995 A | 10/1999 | Shusterman et al. |
| 6,002,952 A | 12/1999 | Diab et al. |
| 6,011,985 A | 1/2000 | Athan et al. |
| 6,036,653 A | 3/2000 | Baba et al. |
| 6,094,592 A | 7/2000 | Yorkey et al. |
| 6,095,984 A | 8/2000 | Amano et al. |
| 6,117,075 A | 9/2000 | Barnea |
| 6,129,675 A | 10/2000 | Jay |
| 6,135,966 A | 10/2000 | Ko |
| 6,151,518 A | 11/2000 | Hayashi |
| 6,163,715 A | 12/2000 | Larsen et al. |
| 6,171,257 B1 | 1/2001 | Weil et al. |
| 6,171,258 B1 | 1/2001 | Karakasoglu et al. |
| 6,181,958 B1 | 1/2001 | Steuer et al. |
| 6,208,951 B1 | 3/2001 | Kumar et al. |
| 6,217,523 B1 | 4/2001 | Amano et al. |
| 6,293,915 B1 | 9/2001 | Amano et al. |
| 6,325,761 B1 | 12/2001 | Jay |
| 6,352,502 B1 | 3/2002 | Chaiken et al. |
| 6,361,501 B1 | 3/2002 | Amano et al. |
| 6,393,311 B1 | 5/2002 | Edgar, Jr. et al. |
| 6,397,096 B1 | 5/2002 | Liu et al. |
| 6,415,166 B1 | 7/2002 | Van Hoy et al. |
| 6,453,184 B1 | 9/2002 | Hyogo et al. |
| 6,510,331 B1 | 1/2003 | Williams et al. |
| 6,516,209 B2 | 2/2003 | Cheng et al. |
| 6,526,301 B2 | 2/2003 | Larsen et al. |
| 6,553,242 B1 | 4/2003 | Sarussi |
| 6,561,986 B2 | 5/2003 | Baura et al. |
| 6,608,934 B2 | 8/2003 | Scheirer et al. |
| 6,654,622 B1 | 11/2003 | Eberhard et al. |

(Continued)

FOREIGN PATENT DOCUMENTS

| | | |
|---|---|---|
| JP | 4332536 | 11/1992 |
| JP | 09-084776 | 3/1997 |
| JP | 2004135854 | 5/2004 |
| JP | 2004194908 | 7/2004 |
| JP | 2004261364 | 9/2004 |
| JP | 3825459 | 4/2005 |
| JP | 2006158974 | 6/2006 |
| JP | 2007267761 | 10/2007 |
| JP | 2007319247 | 12/2007 |
| JP | 2008110108 | 5/2008 |

(Continued)

OTHER PUBLICATIONS

Addison, Paul S., The Illustrated Wavelet Transform Handbook, Taylor & Francis Group, 2002.

(Continued)

*Primary Examiner* — John S Brusca
(74) *Attorney, Agent, or Firm* — Shuats & Leiz LLP

(57) ABSTRACT

According to embodiments, a method and system for artifact detection in signals is disclosed. The artifacts may take the form of movement artifacts in physiological (e.g., pulse oximetry) signals. Artifacts in the wavelet space of the physiological signal may be removed, replaced, ignored, filtered, or otherwise modified by determining the energy within a predefined moving area of the wavelet scalogram, comparing the determined energy within the predefined moving area of the wavelet scalogram to a threshold value, and masking at least one area of artifact in the wavelet scalogram based, at least in part, on the comparison. From the enhanced signal, physiological parameters, for example, respiration, respiratory effort, pulse, and oxygen saturation, may be more reliably and accurately derived or computed.

21 Claims, 18 Drawing Sheets
(4 of 18 Drawing Sheet(s) Filed in Color)

(56) References Cited

U.S. PATENT DOCUMENTS

| | | |
|---|---|---|
| 6,654,623 B1 | 11/2003 | Kastle |
| 6,709,402 B2 | 3/2004 | Dekker |
| 6,748,252 B2 | 6/2004 | Lynn et al. |
| 6,760,610 B2 | 7/2004 | Tschupp et al. |
| 6,773,397 B2 | 8/2004 | Kelly |
| 6,810,277 B2 | 10/2004 | Edgar, Jr. et al. |
| 6,909,912 B2 | 6/2005 | Melker |
| 6,931,269 B2 | 8/2005 | Terry |
| 6,985,762 B2 | 1/2006 | Brashears et al. |
| 7,001,337 B2 | 2/2006 | Dekker |
| 7,020,507 B2 | 3/2006 | Scharf et al. |
| 7,035,679 B2 | 4/2006 | Addison et al. |
| 7,043,293 B1 | 5/2006 | Baura |
| 7,054,453 B2 | 5/2006 | Causevic et al. |
| 7,054,454 B2 | 5/2006 | Causevic et al. |
| 7,079,888 B2 | 7/2006 | Oung et al. |
| 7,171,269 B1 | 1/2007 | Addison et al. |
| 7,173,525 B2 | 2/2007 | Albert |
| 7,203,267 B2 | 4/2007 | De Man et al. |
| 7,209,775 B2 | 4/2007 | Bae et al. |
| 7,222,054 B2 | 5/2007 | Geva |
| 7,225,013 B2 | 5/2007 | Geva et al. |
| 7,254,432 B2 | 8/2007 | Fine |
| 7,254,500 B2 | 8/2007 | Makeig et al. |
| 7,289,835 B2 | 10/2007 | Mansfield et al. |
| 7,309,314 B2 | 12/2007 | Grant et al. |
| 7,341,560 B2 | 3/2008 | Henderson et al. |
| 7,349,727 B2 | 3/2008 | Obata et al. |
| 7,353,054 B2 | 4/2008 | Kawasaki et al. |
| 7,387,607 B2 | 6/2008 | Holt et al. |
| 7,398,115 B2 | 7/2008 | Lynn |
| 7,431,696 B1 | 10/2008 | Brady et al. |
| 7,515,949 B2 | 4/2009 | Norris |
| 7,519,488 B2 | 4/2009 | Fu |
| 7,522,949 B2 | 4/2009 | Berson et al. |
| 7,523,011 B2 | 4/2009 | Akiyama et al. |
| 2001/0051767 A1 | 12/2001 | Williams et al. |
| 2003/0163057 A1 | 8/2003 | Flick et al. |
| 2005/0043616 A1 | 2/2005 | Chinchoy |
| 2005/0070774 A1 | 3/2005 | Addison et al. |
| 2005/0085735 A1 | 4/2005 | Baker et al. |
| 2005/0119708 A1 | 6/2005 | Haefner |
| 2005/0192493 A1 | 9/2005 | Wuori |
| 2005/0197552 A1 | 9/2005 | Baker |
| 2005/0267346 A1 | 12/2005 | Faber et al. |
| 2006/0058595 A1 | 3/2006 | Herrmann |
| 2006/0092029 A1 | 5/2006 | Browne et al. |
| 2006/0155206 A1 | 7/2006 | Lynn |
| 2006/0189880 A1 | 8/2006 | Lynn et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2006/0276697 A1 | 12/2006 | Demuth et al. |
| 2007/0004977 A1* | 1/2007 | Norris ............ 600/336 |
| 2007/0021673 A1 | 1/2007 | Arbel et al. |
| 2007/0027368 A1 | 2/2007 | Collins et al. |
| 2007/0073120 A1 | 3/2007 | Li et al. |
| 2007/0073124 A1 | 3/2007 | Li et al. |
| 2007/0083097 A1 | 4/2007 | Fujiwara et al. |
| 2007/0118028 A1 | 5/2007 | Kitajima et al. |
| 2007/0129647 A1 | 6/2007 | Lynn |
| 2007/0142719 A1 | 6/2007 | Kawasaki et al. |
| 2007/0167694 A1 | 7/2007 | Causevic et al. |
| 2007/0167851 A1 | 7/2007 | Vitali et al. |
| 2007/0213621 A1 | 9/2007 | Reisfeld et al. |
| 2007/0213622 A1 | 9/2007 | Reisfeld |
| 2007/0219439 A1 | 9/2007 | Vilser et al. |
| 2007/0282212 A1 | 12/2007 | Sierra et al. |
| 2007/0299323 A1 | 12/2007 | Arns et al. |
| 2008/0045832 A1 | 2/2008 | McGrath |
| 2008/0076992 A1 | 3/2008 | Hete et al. |
| 2008/0077026 A1 | 3/2008 | Banet et al. |
| 2008/0082018 A1 | 4/2008 | Sackner et al. |
| 2008/0146901 A1 | 6/2008 | Katura et al. |
| 2008/0188733 A1 | 8/2008 | Al-Ali et al. |
| 2008/0200775 A1 | 8/2008 | Lynn |
| 2008/0214903 A1 | 9/2008 | Orbach |
| 2008/0243021 A1 | 10/2008 | Causevic et al. |
| 2008/0262326 A1 | 10/2008 | Hete et al. |
| 2008/0296514 A1 | 12/2008 | Metzger et al. |
| 2009/0326402 A1 | 12/2009 | Addison et al. |

FOREIGN PATENT DOCUMENTS

| | | |
|---|---|---|
| JP | 2008161657 | 7/2008 |
| WO | WO 91/11137 | 8/1991 |
| WO | WO 01/25802 | 4/2001 |
| WO | WO 01/62152 | 8/2001 |
| WO | WO 03/000125 | 1/2003 |
| WO | WO 03/039326 | 5/2003 |
| WO | WO 03/055395 | 7/2003 |
| WO | WO 2004/075746 | 9/2004 |
| WO | WO 2004/105601 | 12/2004 |
| WO | WO 2005/009221 | 2/2005 |
| WO | WO 2005/064314 | 7/2005 |
| WO | WO 2005/096170 | 10/2005 |
| WO | WO 2006/085120 | 8/2006 |
| WO | WO 2006/100685 | 9/2006 |
| WO | WO 2007/048989 | 5/2007 |

OTHER PUBLICATIONS

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Leonard, Paul A., Douglas, J. Graham, Grubb, Neil R., Clifton, David, Addison, Paul S., Watson, James N., "A Fully Automated Algorithm for the Determination of Respiratory Rate From The Photoplethysmogram," Journal of Clinical Monitoring and Computing, 2006.

Yamada, Michio, "Wavelet Analysis and Its Application," Journal of the Institute of Electronics, Information and Communication Engineers, vol. 76, No. 5, May 1993, pp. 518-528.

PCT International Search Report, Applicant's file reference MK/P16360WO, International Application No. PCT/IB2009/006180, International Filing Date Jun. 29, 2009, Priority Date Jun. 30, 2008, Applicant Nellcor Puritan Bennett Ireland.

Samar, V.J. and Bopardiker, A. and Rao, R. and Swartz, K.: "Wavelet analysis of neuroelectric waveforms: a conceptual tutorial" Brain and Language, vol. 66, 1999, pp. 7-60, XP002609090 abstract; figure 4, p. 22, last paragraph—p. 12, p. 18-p. 22, footnote 2, p. 25-p. 26.

Doser A B et al: Transionospheric signal detection with chirped wavelets: Conference Record of the Thirty-First Asilomar Conference on Signals, Systems & Computers, 1997. Pacific Grove, CA, USA 1997. Pacific Grove, CA, USA 1997, Los Alamitos, CA, USA, IEEE Comput. Soc, US, vol. 2, Nov. 2, 1997-Nov. 5, 1997 pp. 1499-1503, XP010280674 DOI: 10.1109/ACSSC.1997.679154 ISBN: 978-0-8186-8316-9 Section 3.

Kyung Hwan Kim et al: "A wavelet-based method for action potential detection from extracellular neural signal recording with low signal-to-noise ratio" IEEE Transactions on Biomedical Engineering, IEEE Service Center, Piscataway, NJ, US LNKD-DOI:10.1109/TBME.2003.814523, vol. 50, No. 8, Aug. 1, 2003, p. 999-1011, XP011098741, ISSN: 0018-9294, Section III.A.

(56) References Cited

OTHER PUBLICATIONS

Nakatani* H et al: "Detection of Nerve Action Potentials Under Low Signal-To-Noise Ratio Condition" IEEE Transactions on Biomedical Engineering, IEEE Service Center, Piscataway, NJ, US, vol. 48, No. 8, Aug. 1, 2001, XP011007119, ISSN: 0018-9294, Section D.

Clarencon, D. et al.: "Real-time spike detection in EEG signals using the wavelet transform and a dedicated digital signal processor card" Journal of Neuroscience Methods, vol. 70, No. 1, 1996, pp. 5-14, XP002609091, Sections 3, 4 figures 7-9.

Senhadji L et al: "Interictal EEG spike detection: a new framework based on wavelet transform" Proceedings of the IEEE on Time-Frequency and Time-Scale Analysis, 1994., New York, NY, USA, IEEE, US, Oct. 25, 1994-Oct. 28, 1994 pp. 548-551, XP002609092 DOI: 10.1109/TFSA.1994.467293 ISBN: 978-0-7083-2127-4, p. 548-p. 549.

Chan H L et al: Detection of neuronal spikes using an adaptive threshold based on the max-min spread sorting method: Journal of Neuroscience Methods, vol. 172, No. 1, Jul. 15, 2008, pp. 112-121, XP022698376, Elsevier Science Publisher B.V., Amsterdam, NL ISSN: 0165-0270 DOI: 10.1016/J. Jneumeth.2008.04.014 [retrieved on Apr. 22, 2008] Section 2.1.

Christov Ivaylo I: "Real time electrocardiogram QRS detection using combined adaptive threshold" Biomedical Engineering Online, vol. 3, No. 1, Aug. 27, 2004, p. 28, XP021007742, Biomedcentral Ltd, London, GB ISSN: 1475-925X-3-28, abstract p. 3-p. 5.

* cited by examiner

600

610

1100

| Power Representation | Variable Description | Neonatal Value | Adult Value |
|---|---|---|---|
| Ridge Power | Percentile of power used in global threshold | 20 | 20 |
| | Global threshold multiple | 2.5 | 0.2 |
| | Global window length | 60 secs | 60 secs |
| Wedge Power | Percentile of power used in local threshold | 5 | 5 |
| | Local window length | 10 secs | 10 secs |
| | Local threshold multiple | 1.2 | 1.2 |
| | Charateristic frequency of minumum scale | 0.6 Hz | 0.4 |
| | Charateristic frequency of maximum scale | 2.00 Hz | 0.67 |
| | Multiple of a scale for wedge width ($k$) | 1 | 1 |

FIG. 11

SYSTEMS AND METHODS FOR ARTIFACT DETECTION IN SIGNALS

CROSS-REFERENCE TO RELATED APPLICATIONS

This claims the benefit of U.S. Provisional Patent Application Nos. 61/076,934, entitled "Systems and Methods for Artifact Detection in Signals" and 61/077,130, entitled "Systems and Methods of Signal Processing," both filed Jun. 30, 2008, which are hereby incorporated by reference herein in their entireties.

SUMMARY

The present disclosure relates to signal processing and, more particularly, the present disclosure relates to using continuous wavelet transforms for processing, for example, a photoplethysmograph (PPG) signal.

As described in more detail below, a pulse oximeter may be used to determine oxygen saturation by an analysis of an optically sensed plethysmograph. The oximeter may pass light using a light source through blood perfused tissue and photoelectrically sense the absorption of light in the tissue.

The optical signal through the tissue, however, can be degraded by many sources of noise. One source of noise may include ambient light which reaches the light detector. Another source of noise may include electromagnetic coupling or interference from other electronic instruments. Movement of the patient also introduces noise and may affect the optical signal. For example, the contact between the light detector and the skin (or the light emitter and the skin) can be temporarily disrupted when a patient's movement causes either the detector or emitter to move temporarily away from the skin. In addition, since blood is a fluid, it responds differently than the surrounding tissue to inertial effects, thus resulting in momentary changes in volume at the point to which the oximeter probe is attached. This may introduce yet another source of noise in the optical signal, resulting in degradation of the optical signal. Any of the aforementioned sources of noise may result in the presence of movement artifact in the detected optical signal.

Although the present disclosure refers to PPG signals for illustrative purposes, the present disclosure is applicable to any suitable signals. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In particular, an analysis of the energy density function of the wavelet transform of a signal (also called the scalogram of the signal) is useful in many applications, including the measurement of physiological parameters. In one example, a physiological measurement system may take a pulse oximetry signal from a patient and then analyze the pulse oximetry signal to measure, derive, or compute one or more physiological parameters. These physiological parameters may include, for example, pulse rate, respiration rate, respiratory effort, oxygen saturation, and physical movement of the patient. For example, in sleep studies, movement may be monitored for patients with, for example, restless leg syndrome. According to embodiments of the present disclosure, noise and noise artifacts may be detected in the physiological signal (e.g., the pulse oximetry signal) or the scalogram of such a signal. Artifacts may also be detected in any rescaled scalogram.

After an artifact is detected, the artifact may be removed, ignored, or filtered from the physiological signal (or the scalogram of the physiological signal) to yield a signal with reduced artifact noise. For example, movement or muscle artifacts may be removed, ignored, or filtered to enhance the signal prior to, during, or after analysis. From the enhanced signal, more accurate and reliable physiological parameters may be determined. In an embodiment, movement or muscle artifact may be monitored and used as clinically useful information. For example, this information may indicate arousal or restless leg syndrome.

In some embodiments, the energy within one or more areas of the scalogram of a physiological signal may be calculated. The shape and size of the area or areas (e.g., generally wedge shaped areas) may be based on one or more characteristics of the artifact being detected. The characteristics of some types of artifacts may scale according to the characteristic frequencies of the wavelets. In one example, the area may be generally a wedge shape where the width of the wedge is smaller at small wavelet scales and larger at large wavelet scales. A movement artifact of a PPG signal may be one such example of an artifact with a generally wedge shaped artifact area in the scalogram of the PPG signal.

In an embodiment, a single area may be used to measure energy within one continuous range of scales within the scalogram (e.g., between the breathing band and the pulse band), or multiple areas may be used at different ranges of scales and times. The energy of the area may then be compared to a threshold energy level. The threshold energy level may be based on the previously detected energy measurements (e.g., a running or moving average of previously detected energy measurements), the energy of the pulse band, a predetermined threshold, and/or any combination thereof. When an artifact is detected, the data within the area of the artifact may be ignored, replaced, or otherwise filtered from the physiological signal (or the scalogram of the physiological signal), resulting in an enhanced signal (or enhanced scalogram). This enhanced signal (or enhanced scalogram) may then be used to determine physiological parameters more reliably and with less error.

In some embodiments, the threshold energy value is based on at least two components, a local wavelet component and a global wavelet component. The local wavelet component may be derived from the energy within a predefined moving area of the wavelet scalogram over a first time window, and the global wavelet component may be derived from a second energy measure (e.g., the pulse ridge energy) over a second time window, wherein the second time window is longer than the first time window. In some embodiments, the threshold energy value may be additionally or alternatively based on a running or moving average energy level within a predefined moving area or the wavelet scalogram.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which:

FIG. 11 is an illustrative table of artifact detection settings for adult/child and neonatal signals in accordance with an embodiment;

DETAILED DESCRIPTION

Figure 1:
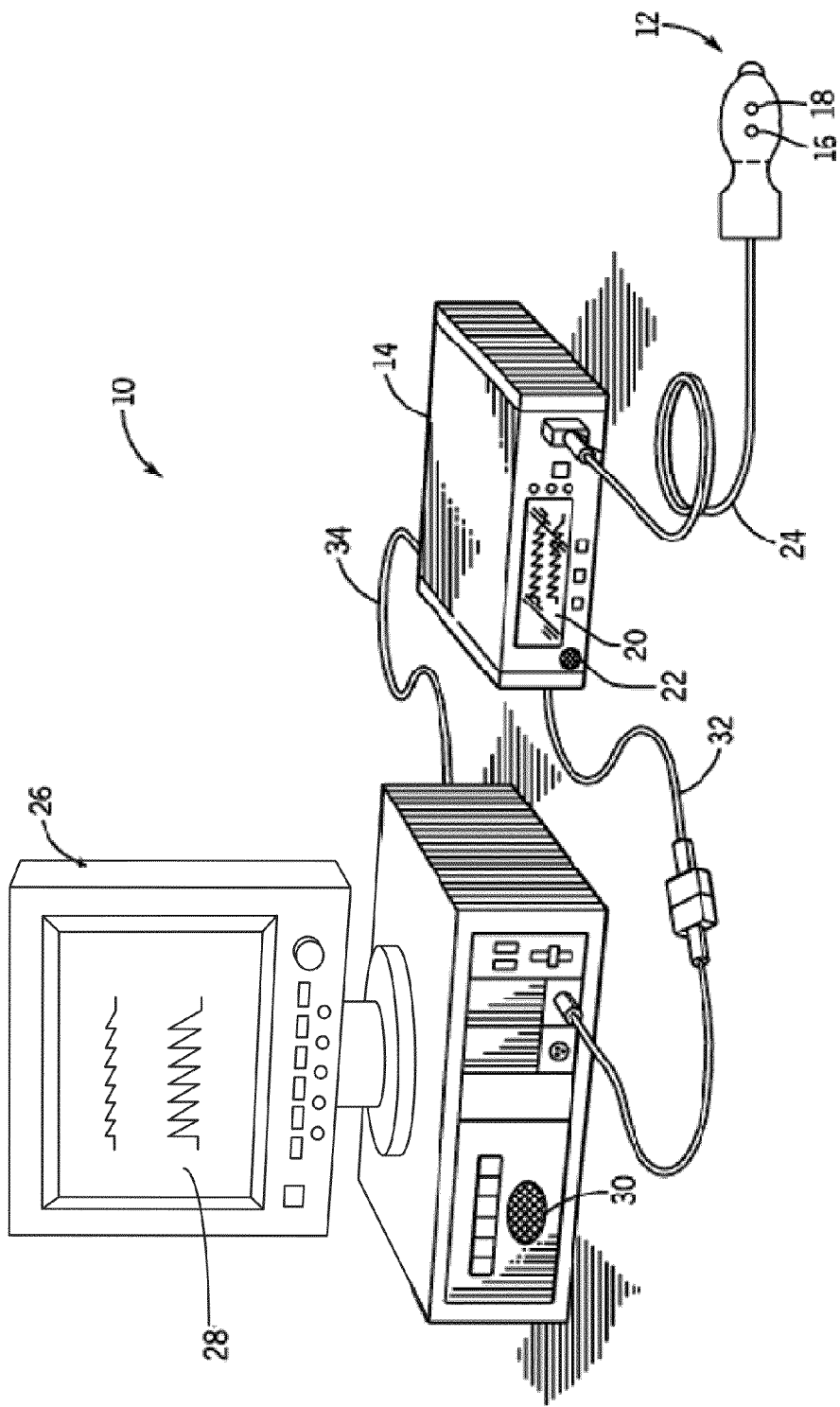
FIG. 1 shows an illustrative pulse oximetry system in accordance with an embodiment.

The detection of artifacts (e.g., movement artifacts) in all types of signals (e.g., physiological signals, such as PPG signals) may be important for the selection and/or calculation of clean signal segments used in the determination of various parameters derived from the signal (e.g., physiological parameters derived from a PPG signal). In the physiological realm, these parameters may include, for example, pulse rate, respiration rate, respiratory effort, and oxygen saturation. In addition, artifact detection, such as movement artifact detection, may form an important part of a comprehensive neonatal respiration and movement monitoring device.

An oximeter is a medical device that may determine the oxygen saturation of the blood. One common type of oximeter is a pulse oximeter, which may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \qquad (1)$$

where:

$\lambda$=wavelength;

t=time;

I=intensity of light detected;

$I_o$=intensity of light transmitted;

s=oxygen saturation;

$\beta_o,\beta_r$=empirically derived absorption coefficients; and l(t)=a combination of concentration and path length from emitter to detector as a function of time.

The traditional approach measures light absorption at two wavelengths (erg, red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R) + (1-s)\beta_r(\lambda_R)}{s\beta_o(\lambda_{IR}) + (1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR}) - \beta_r(\lambda_{IR})) - \frac{d\log I(\lambda_{IR})}{dt}(\beta_o(\lambda_R) - \beta_r(\lambda_R))}$$

Note in discrete time $$\frac{d\log I(\lambda, t)}{dt} \simeq \log I(\lambda, t_2) - \log I(\lambda, t_1)$$

Using log A−log B=log A/B, $$\frac{d\log I(\lambda, t)}{dt} \simeq \log\left(\frac{I(t_2, \lambda)}{I(t_1, \lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1, \lambda_R)}{I(t_2, \lambda_R)}\right)}{\log\left(\frac{I(t_1, \lambda_{IR})}{I(t_2, \lambda_{IR})}\right)} = R, \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method uses a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2, \lambda_R) - I(t_1, \lambda_R)}{I(t_1, \lambda_R)}}{\frac{I(t_2, \lambda_{IR}) - I(t_1, \lambda_{IR})}{I(t_1, \lambda_{IR})}} \quad (7)$$

$$= \frac{[I(t_2, \lambda_R) - I(t_1, \lambda_R)]I(t_1, \lambda_{IR})}{[I(t_2, \lambda_{IR}) - I(t_1, \lambda_{IR})]I(t_1, \lambda_R)}$$

$$= R$$

which defines a cluster of points whose slope of y versus x will give R where $$x(t) = [I(t_2, \lambda_{IR}) - I(t_1, \lambda_{IR})]I(t_1, \lambda_R)$$

$$y(t) = [I(t_2, \lambda_R) - I(t_1, \lambda_R)]I(t_1, \lambda_{IR}) \quad (8)$$

$$y(t) = Rx(t)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patients forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "$SpO_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
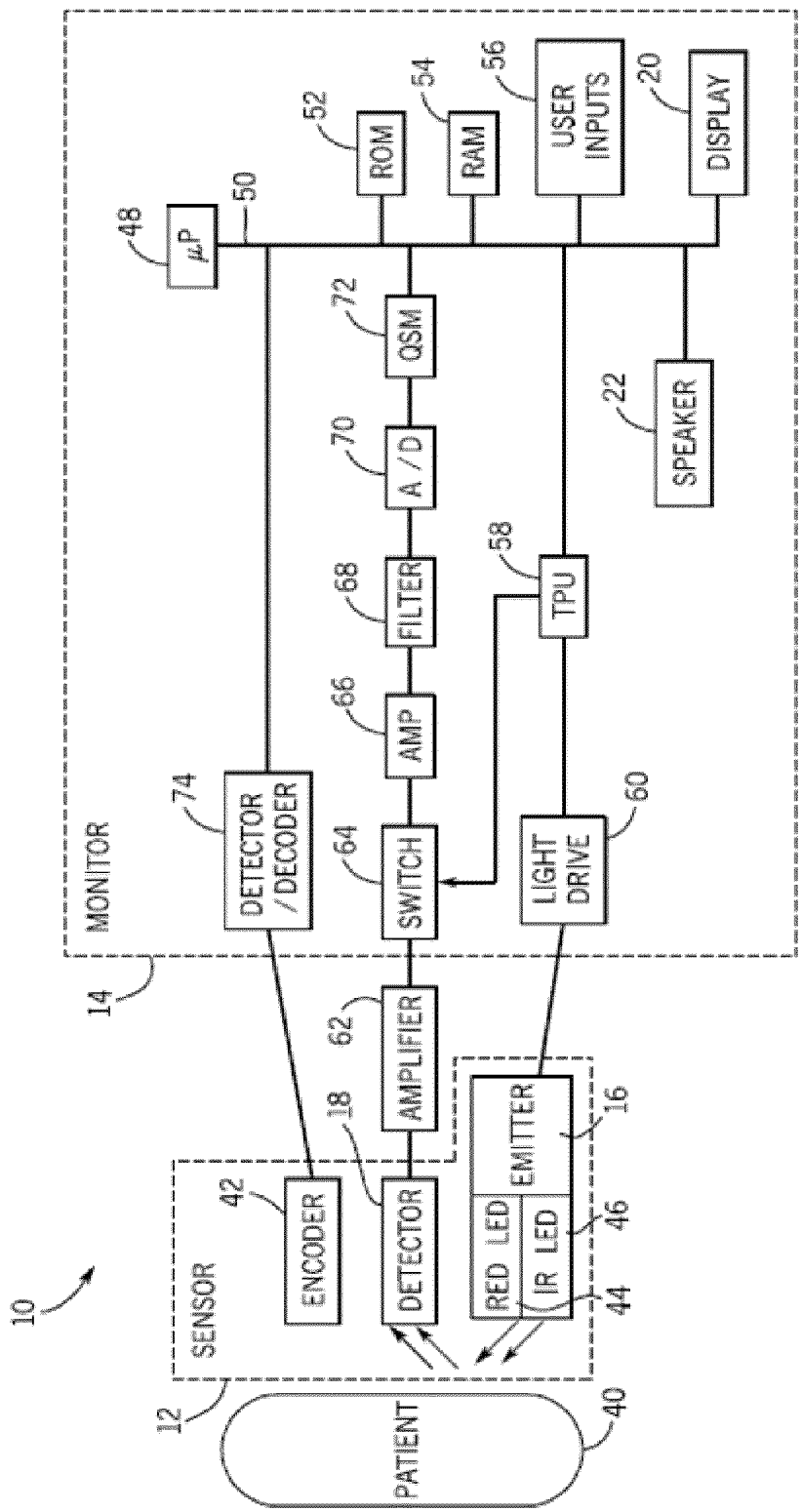
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40.

Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/ID converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t)\psi^*\left(\frac{t-b}{a}\right) dt \quad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \quad (10)$$

where '||' is the modulus operator. The scalogram may be rescaled for useful purposes. One common rescaling is defined as $$S_R(a,b) = \frac{|T(a,b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required scale and then multiplying the result by $\sqrt{a}$.

In the discussion of the technology which follows herein, the "scalogram" may be taken to include all suitable forms of rescaling including, but not limited to, the original unscaled wavelet representation, linear rescaling, any power of the modulus of the wavelet transform, or any other suitable rescaling. In addition, for purposes of clarity and conciseness, the term "scalogram" shall be taken to mean the wavelet transform, $T(a,b)$ itself, or any part thereof. For example, the real pair of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at $a=1$), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t)=\pi^{-1/4}(e^{i2\pi f_0 t}-e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
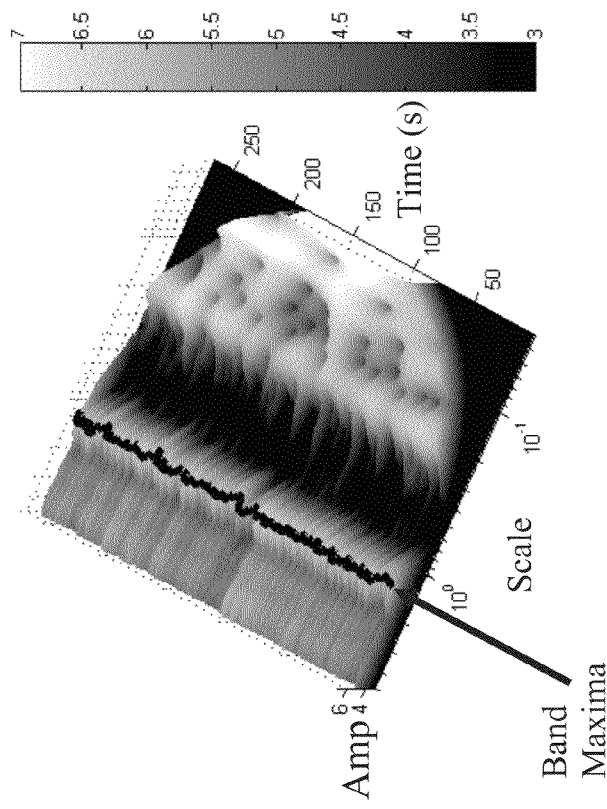
FIGS. 3(a) and 3(b) show illustrative views of a scalogram derived from a PPG signal in accordance with an embodiment.
Figure 3A:
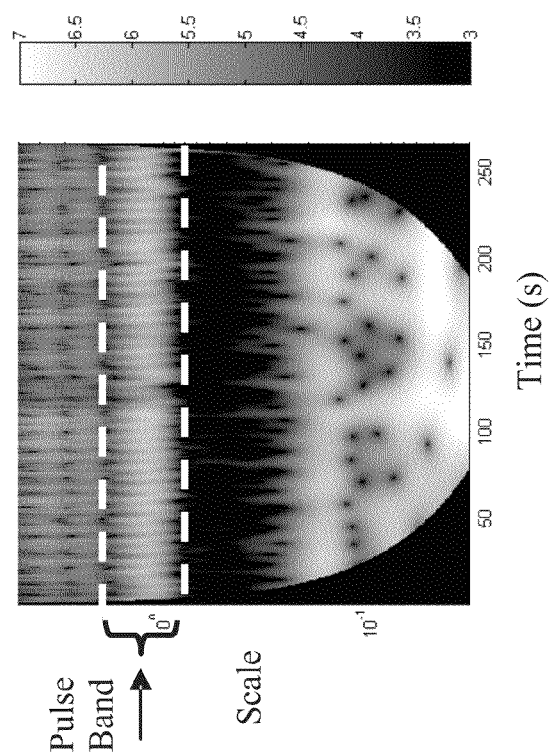

Pertinent repeating features in a signal give rise to a time-scale band in wavelet space or a rescaled wavelet space. For example, the pulse component of a PPG signal produces a dominant band in wavelet space at or around the pulse frequency. FIGS. 3(a) and (b) show two views of an illustrative scalogram derived from a PPG signal, according to an embodiment. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable rescaling of the scalogram, such as that given in equation (11), the ridges found in wavelet space may be related to the instantaneous frequency of the signal. In this way, the pulse rate may be obtained from the PPG signal. Instead of rescaling the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
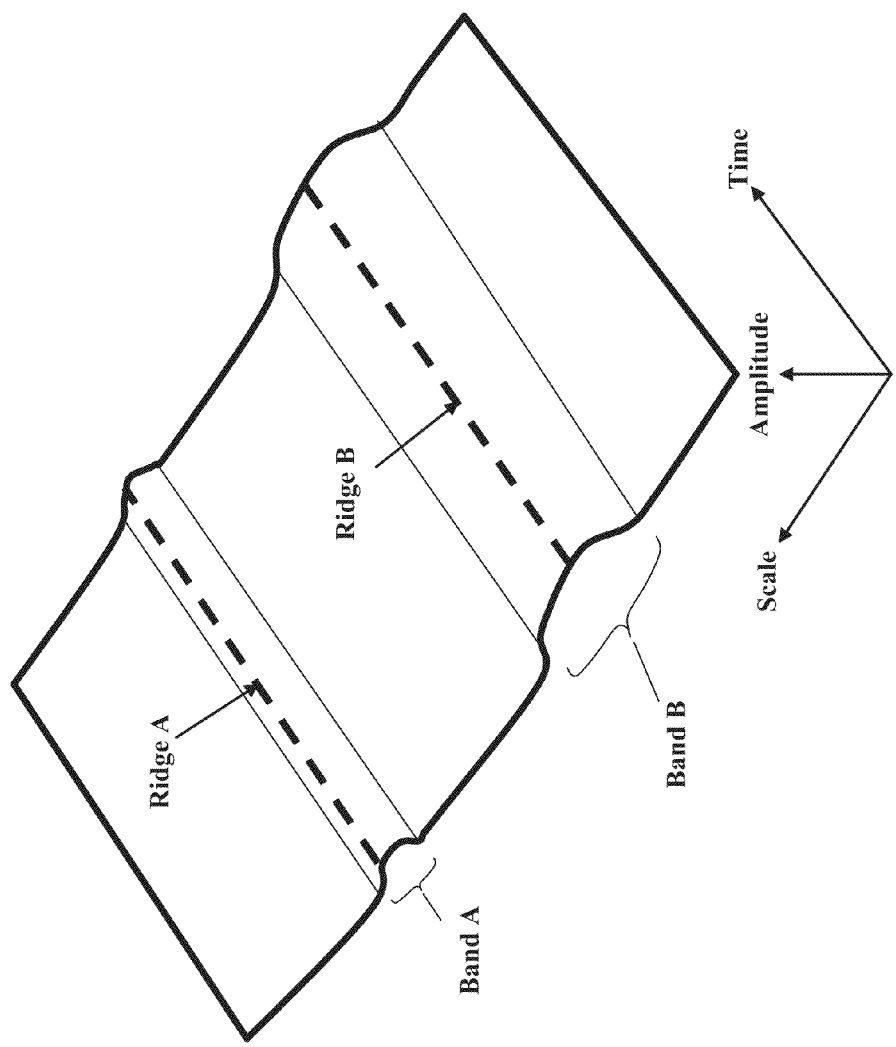
FIG. 3(c) shows an illustrative scalogram derived from a signal containing two pertinent components in accordance with an embodiment.
Figure 3D:
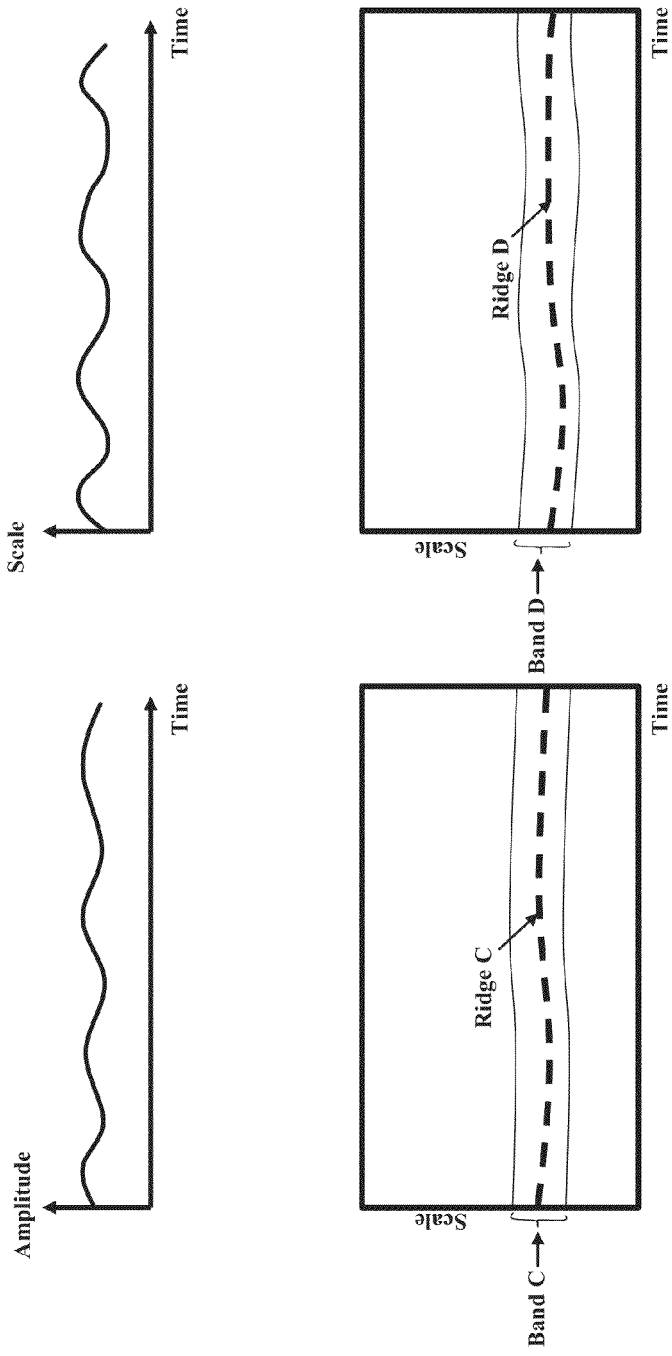
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a rescaled wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a, b) \frac{1}{\sqrt{a}} \psi\left(\frac{t-b}{a}\right) \frac{da\, db}{a^2} \quad (15)$$

which may also be written as:

$$x(t) = \frac{1}{C_g} \int_{-\infty}^{\infty} \int_0^{\infty} T(a, b) \psi_{a,b}(t) \frac{da\, db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
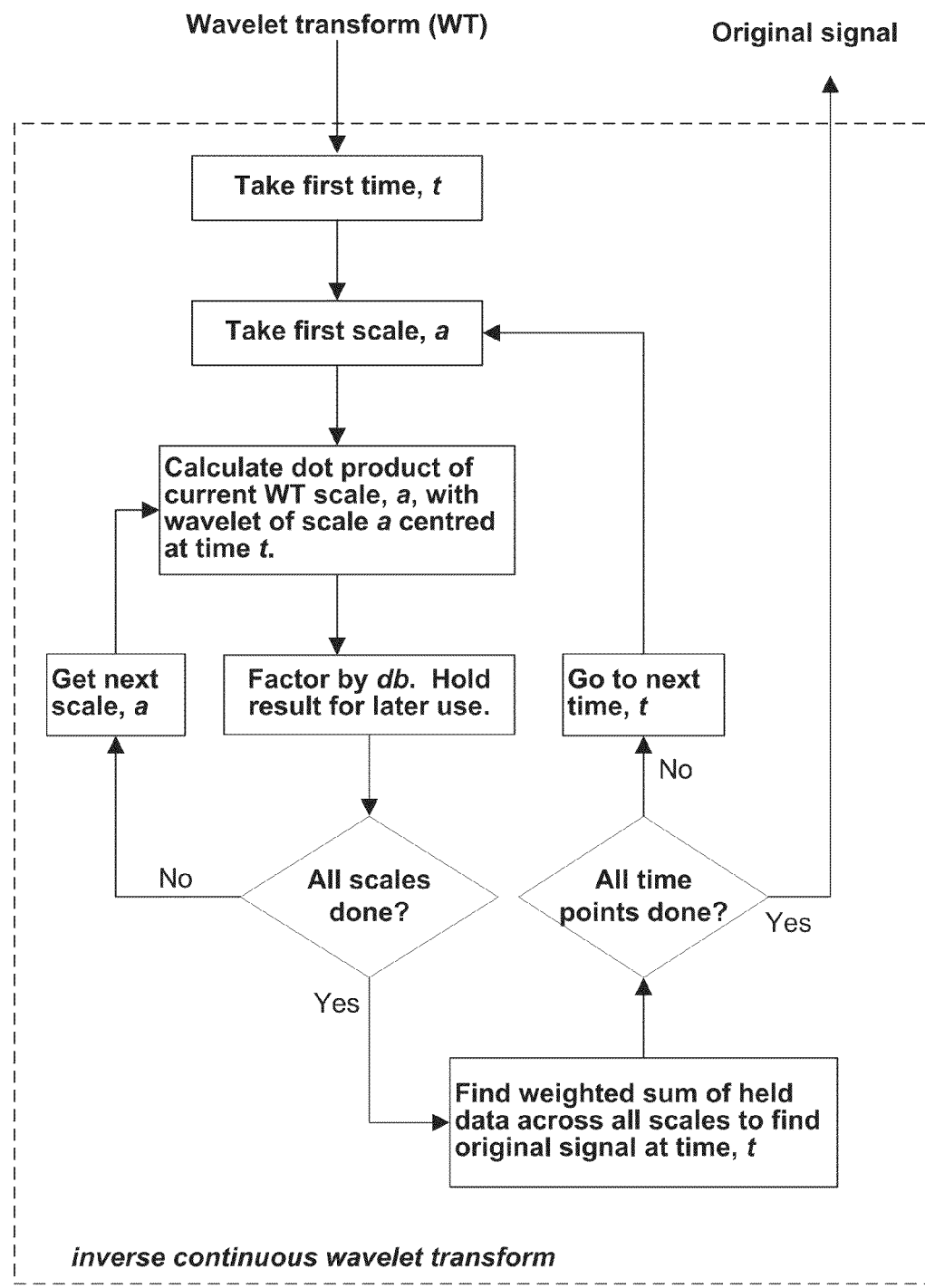
FIGS. 3(e) and 3(f) are flow charts of illustrative steps involved in performing an inverse continuous wavelet transform in accordance with embodiments.
Figure 3F:
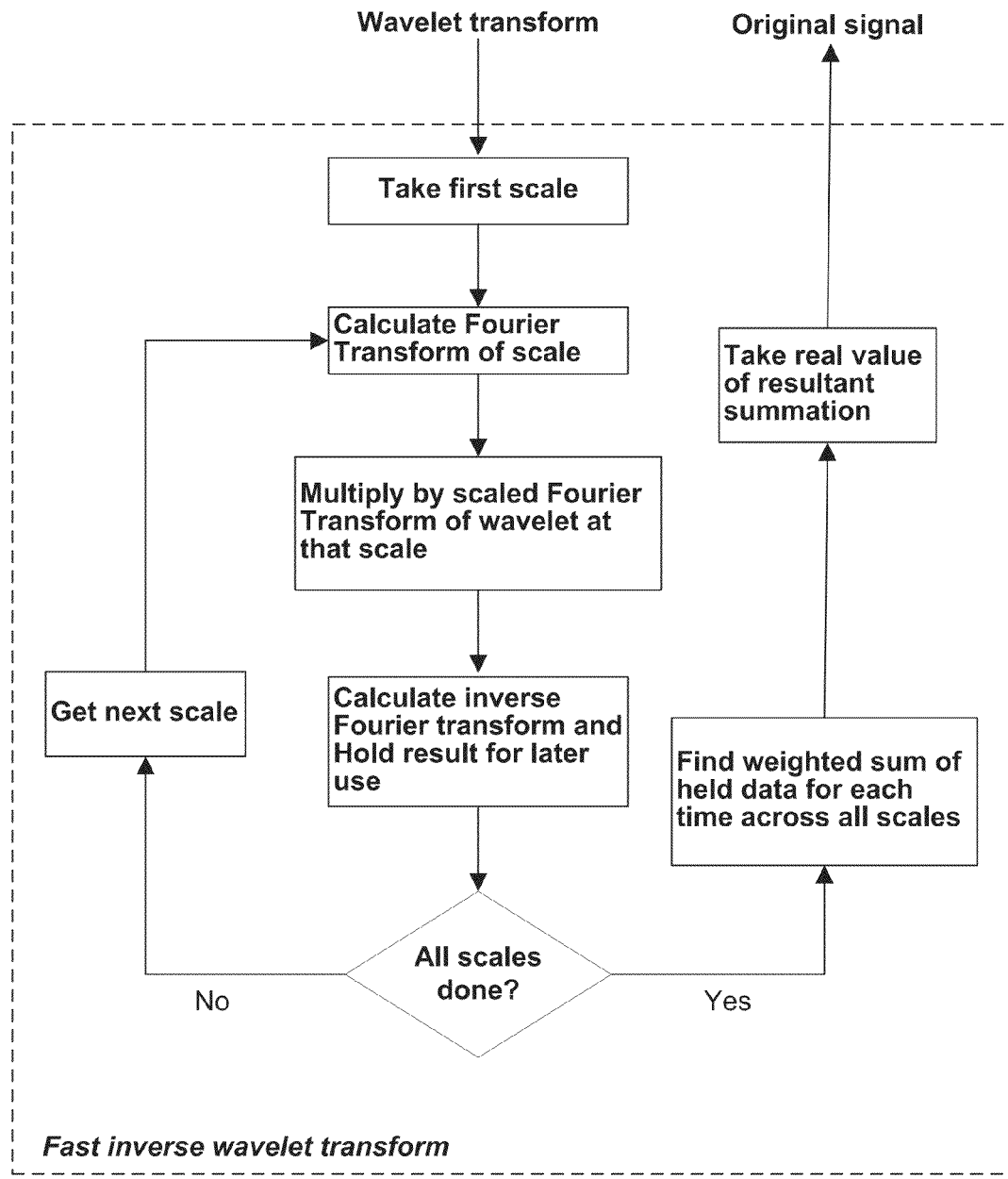

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
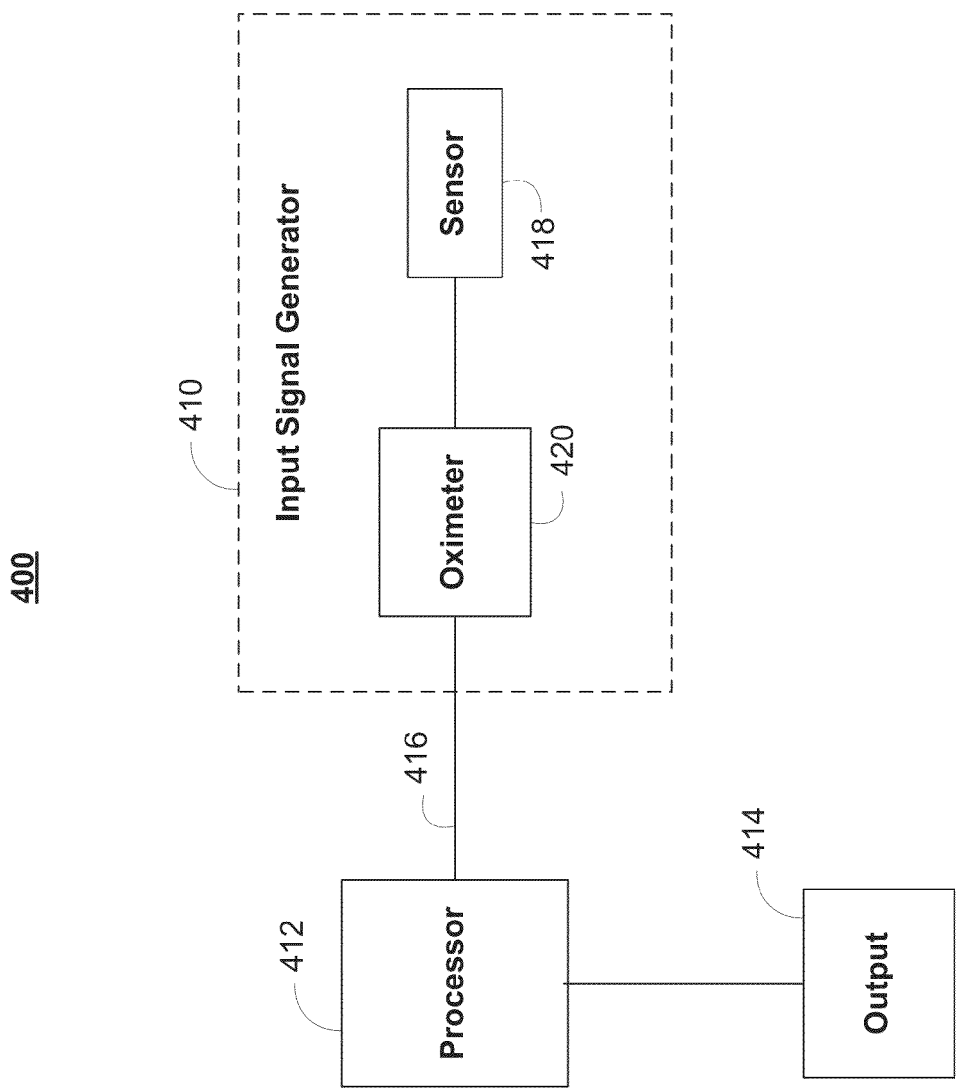
FIG. 4 is a block diagram of an illustrative continuous wavelet processing system in accordance with some embodiments.

FIG. 4 is an illustrative continuous wavelet processing system 400 in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms.

For example, processor 412 may determine the energy within one or more predefined moving areas of any suitable wavelet scalogram derived from signal 416, compare the determined energy within the predefined moving area of the wavelet scalogram to a threshold value, and determine whether to modify the wavelet scalogram based at least in part on the comparison in order to reduce or minimize artifact noise. Processor 412 may also create a scalogram mask, as described in more detail below, in order to filter or remove artifact noise. An enhanced wavelet scalogram may then be generated using the scalogram mask. From the enhanced wavelet scalogram, more reliable parameters (e.g., physiological parameters) may be determined or derived. Processor 412 may also perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etc.), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof, one or more printing devices, any other suitable output device, or any combination thereof.

It will be understood that system 400 may be incorporated into system 10 (FIGS. 1 and 2) in which, for example, input signal generator 410 may be implemented as palls of sensor 12 and monitor 14 and processor 412 may be implemented as part of monitor 14.

In an embodiment, system 400 (FIG. 4) and system 10 (FIGS. 1 and 2) may use one or more scalograms derived from one or more PPG signals to calculate physiological parameters such as pulse rate, respiration rate, respiration effort, and oxygen saturation. As discussed above, the pulse component of a PPG signal may produce a dominant band in a scalogram. The pulse rate may be determined, for example, by following or identifying the ridge of the pulse band, identifying the scale corresponding to the ridge, and selecting the pulse rate to be the characteristic frequency of the identified scale. Similarly, respiration rate may be determined based on the ridge of the respiration band in a scalogram. Respiration rate may also be determined by performing a secondary wavelet decomposition of modulations of the pulse band. Techniques for determining respiration rate from one or more scalograms are described in more detail in Addison et al. U.S. Pat. No. 7,035,679, which is hereby incorporated by reference herein in its entirety. Oxygen saturation may be determined, for example, by computing the ratio of points on two scalograms (e.g., at the location of the pulse band) and using, for example, a lookup table or an equation to obtain oxygen saturation. This process and other processes for determining oxygen saturation from scalograms is described in more detail in Addison et al. U.S. Patent App. Pub. No. 2006/0258921 A1, which is hereby incorporated by reference herein in its entirety. Respiratory effort may be determined, for example, by measuring the energy within a region of the scalogram respiration associated with the respiration band and also by analyzing the modulation of the pulse ridge. Techniques for determining respiratory effort are described in more detail in U.S. Provisional Patent Application No. 61/077,097, filed Jun. 30, 2008 and U.S. patent application Ser. No. 12/245,366, filed Oct. 3, 2008, which are hereby incorporated by reference herein in their entireties.

Artifacts, such as movement artifacts, may affect a wide range of signals and virtually all PPG signals. Movement may be observed generally in a signal as any significant movement of, or change in, the detected signal. As described above, movement may be caused, at least in part, by one or more sources of noise affecting the signal. Detection of movement artifacts in wavelet transforms of physiological signals may be particularly useful for more reliable determination of physiological parameters.

Figure 5:
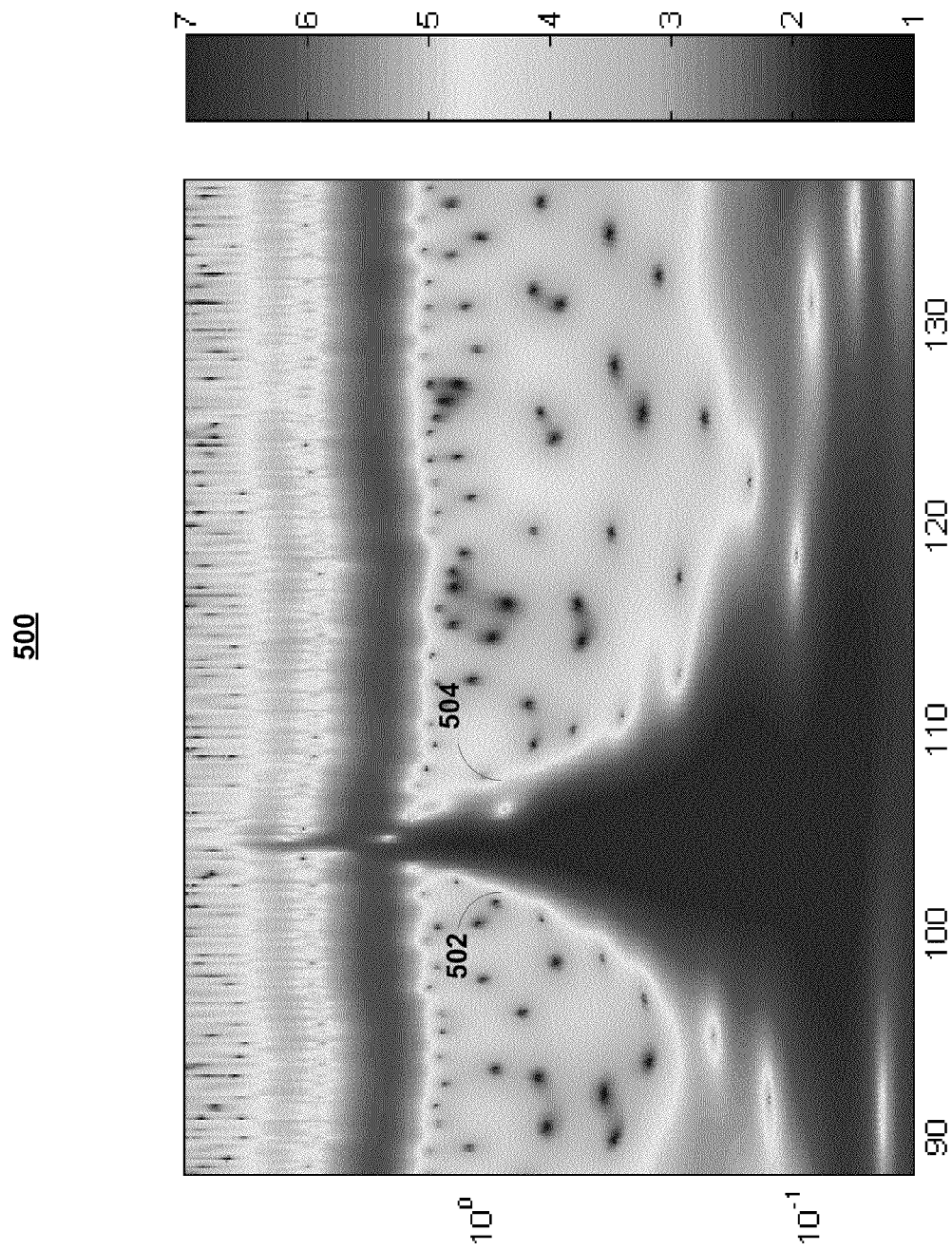
FIG. 5 is an illustrative scalogram showing the manifestation of a movement artifact in the time-scale plane in accordance with an embodiment.

Movement generally exhibits broadband activity across the wavelet transform surface localized in time. The region of influence across wavelet space of a short duration movement artifact in wavelet space is generally proportional to the wavelet scale. FIG. 5 shows plot 500, which may be a typical plot of the manifestation of a movement artifact in the wavelet plane, according to an embodiment. Boundaries 502 and 504 of the artifact feature may be curved outwards due to the logarithmic scale used as part of the continuous wavelet transform.

To detect movement within the physiological signal (i.e., via its wavelet transform representation), a recognizable feature or group of features associated with movement may first be determined.

To determine the recognizable feature or group of features associated with movement, two candidate power signals may be derived from the scalogram and a third power signal may be derived from the original physiological (e.g., PPG) signal. These power signals may then be inspected for characteristic signs of movement in the original signal. In an embodiment, the power signals may include one or more of the following power signals: (1) a localized signal power measure; (2) a power signal derived from the pulse ridge amplitude in resealed wavelet space; and (3) a wavelet power measure derived from a sliding wedge window. Although these measures are sometimes referred to as power measures herein, corresponding energy measures may also be used.

Figure 6A:
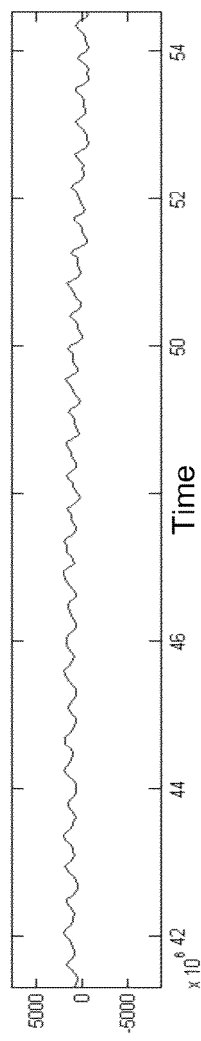
FIG. 6(a) shows an illustrative signal segment without movement artifact in accordance with an embodiment.
Figure 6B:
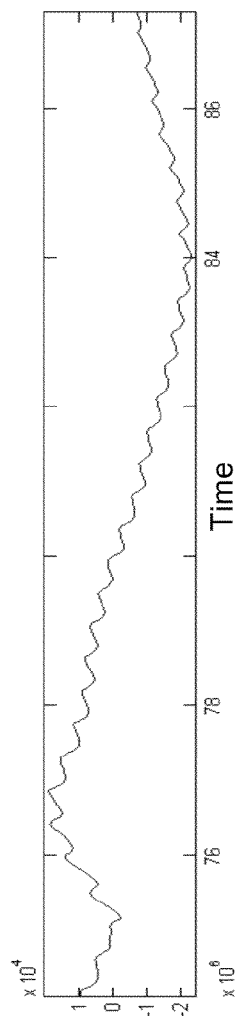
FIG. 6(b) shows an illustrative signal segment with movement artifact in accordance with an embodiment.

In an embodiment, the localized signal power measure may include energy per unit time defined as $$P_s(t) = \frac{\int_{t-T}^{t} |x(t) - \bar{x}_T|^2 dt}{T} \quad (18)$$

which measures the power within the signal over a predefined window of length T where the signal within the window is first subtracted from its mean $\bar{x}_T$. This measure has the advantage that disturbances caused by movement cause local signal slopes across the whole window, thus greatly increasing its value. Thus, the segment of "quiet" signal shown in signal 600 of FIG. 6(a) will have a lower $P_s$ value than that of signal 610 of FIG. 6(b), which contains movement artifact, although both have pulse components of about the same amplitude.

Figure 7:
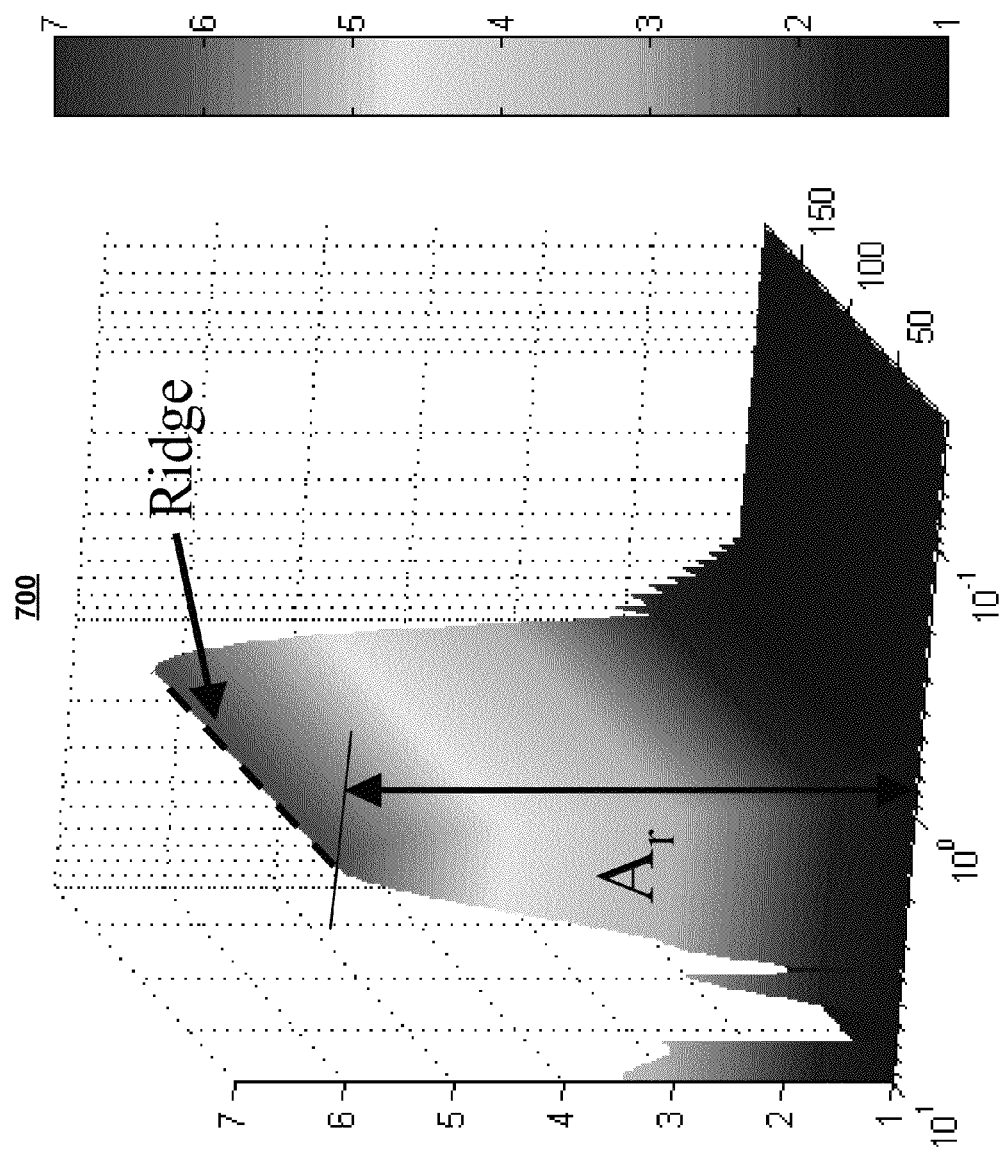
FIG. 7 shows an illustrative graph of the amplitude of a ridge corresponding to a sinusoidal signal in accordance with an embodiment.

In an embodiment, the pulse ridge power may be reflected by the resealed scalogram, $S_R(a,b)$, which may be used in the time-scale representation. It can be shown for this resealing that the amplitude of a ridge, $A_r$, on the surface of this representation, (shown in representation 700 of FIG. 7) generated from the wavelet may be approximately related to the signal amplitude $A_s$ by the relationship $$A_r = \sqrt{\pi}(A_s)^2 \quad (19)$$

In addition, for example, for a sinusoidal signal, the energy in the signal per unit time is equal to $(A_s)^2/2$. Hence, the signal power in terms of the wavelet ridge may be defined as $$P_r(t) = \frac{A_r(t)}{2\sqrt{\pi}} \quad (20)$$

Figure 8:
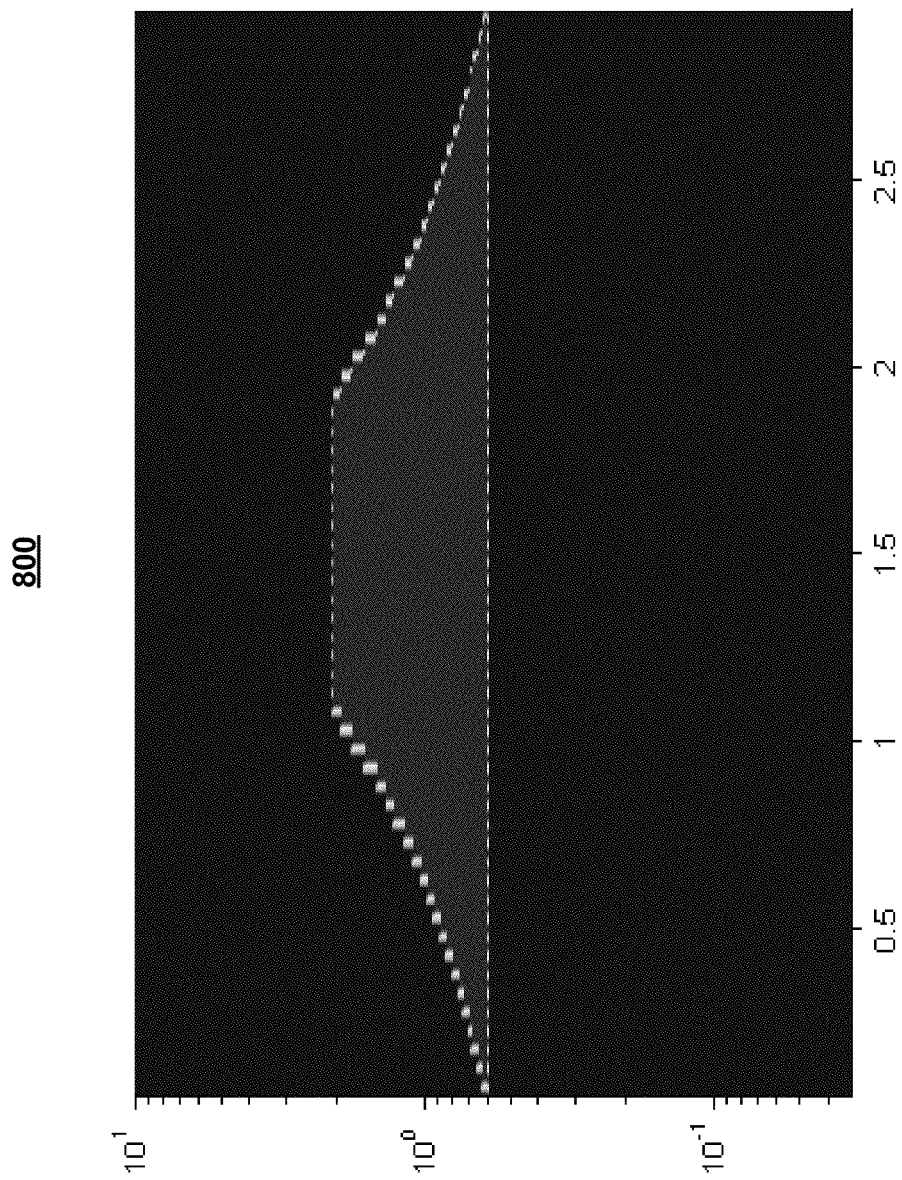
FIG. 8 shows an illustrative generally wedge shaped region used to ignore, replace, or filter a movement artifact in accordance with an embodiment.

In an embodiment, to compute the wavelet wedge power, selected regions of wavelet space may be probed. To probe selected regions of wavelet space within an artifact wedge region, the energy per unit time in a sliding wedge window region may be defined as $$P_w(t) = \int_{a_{min}}^{a_{max}} \frac{\left[\int_{t-ka}^{t+ka} \frac{|T(a,b)|^2}{a^2 C_g} db\right]}{2ka} da \quad (21)$$

where the wedge width 2ka is defined in terms of a multiple of scale and k is a constant which controls the rate of wedge width over scales. FIG. 8 shows illustrative wedge region 800 defined by wavelet scales with characteristic frequencies of 0.6 to 2.0 Hz and a k of unity.

Figure 9A:
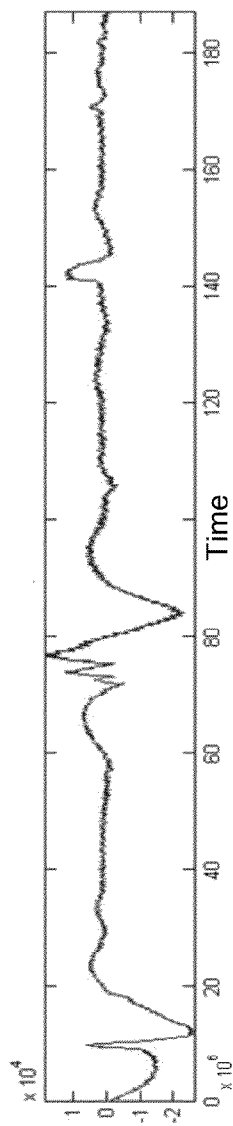
FIG. 9(a) shows an illustrative PPG signal in accordance with an embodiment.
Figure 9B:
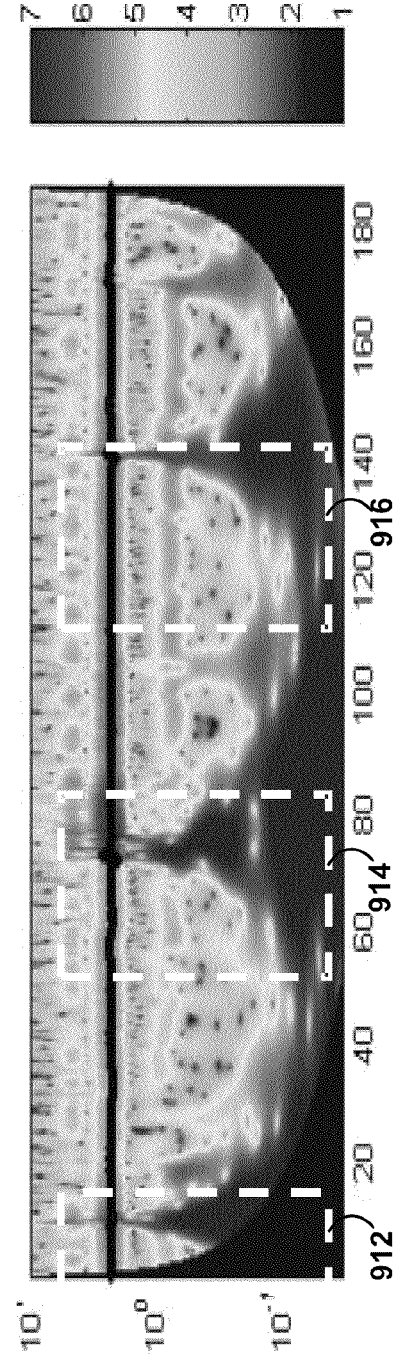
FIG. 9(b) shows the corresponding wavelet scalogram of the PPG signal shown in FIG. 9(a) in accordance with an embodiment.
Figure 9C:
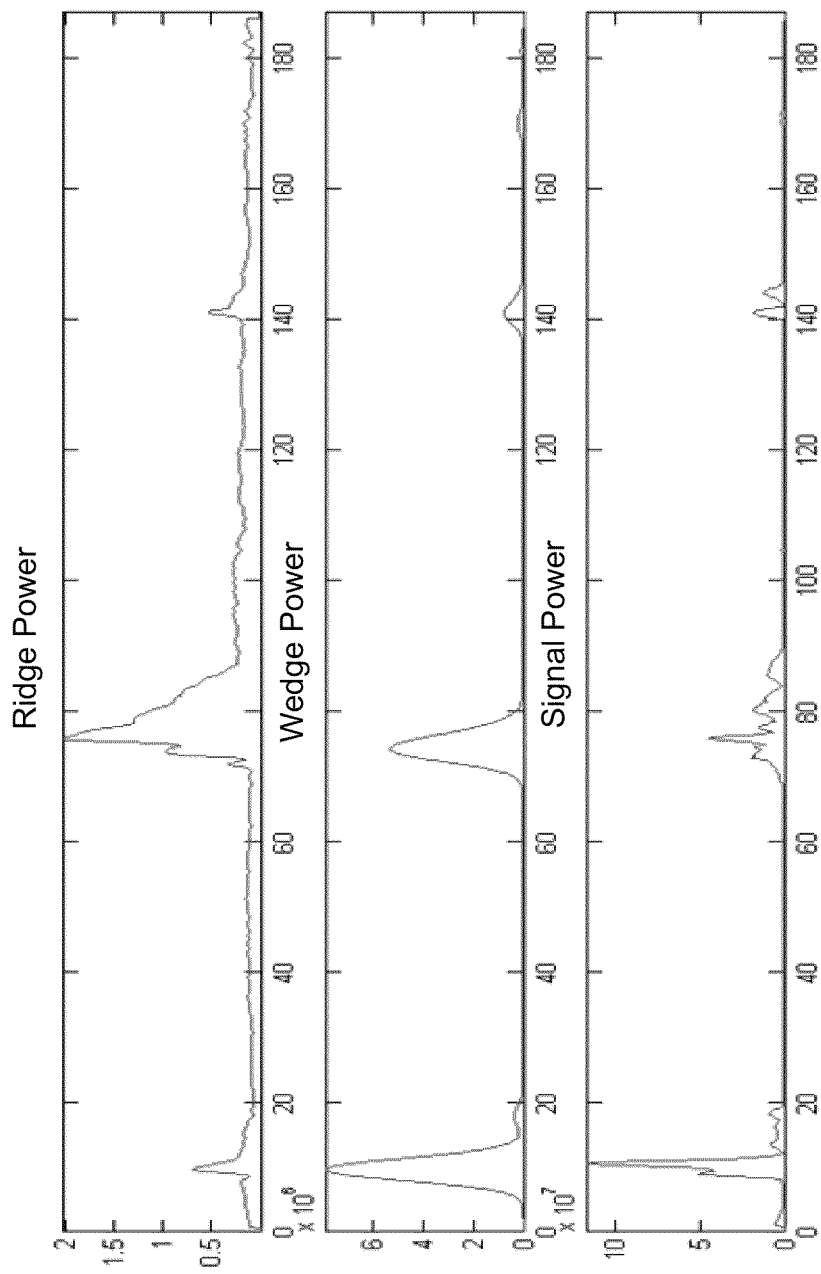
FIG. 9(c) shows illustrative plots of ridge power, wedge power, and signal power of the signal and scalogram shown in FIGS. 9(a) and 9(b) in accordance with an embodiment.

Plot 900 of FIG. 9(a) shows an illustrative three minute segment of an infra-red (IR) PPG signal acquired from a neonate, according to an embodiment. A number of artifacts are apparent in the signal. Wavelet transform plot 910 (FIG. 9(b)) of the signal shown in FIG. 9(a) is shown below the IR PPG signal. The movement artifact regions are indicated within dashed boxes 912, 914, and 916. The three power representations described above are shown in FIG. 9(c). All three power representations may be interrogated to provide a movement detector. To do this, the local excursions in one or more of the power representations may be detected.

From studying the behavior of the three power measures (i.e., the localized signal power measure, the power signal derived from the pulse ridge amplitude in resealed wavelet space, and the wavelet power measure derived from a sliding wedge window), the sliding wedge window power measure may provide the signal with the most separation between the clean and artifact parts of the signal. In fact, some signals (for the wedge scale range chosen) may even exhibit a near zero value of wedge energy in the clean regions.

In some embodiments, the movement artifact detection process may use a moving threshold value along the signal whereby movement regions may be defined as those segments where the wedge power signal increases beyond the moving threshold value. Conversely, clean regions may be defined as those regions where the wedge power signal is below the moving threshold value.

Setting a suitable moving threshold value may be performed in a number of ways. For example, in some embodiments, a number of candidate thresholds based, at least in part, on one or more of the power representations (described above) may be used. In some embodiments, the threshold may additionally or alternatively be based, at least in part, on a low percentile (e.g., 5 to 20%) of the signal energy over a preceding time window. In such embodiments, the threshold may then be computed as some multiple of this level.

This technique for determining the moving threshold may be robust for regions with no movement or with a single localized movement spike. However, for regions where multiple movements occur over a period beyond the local window, the moving threshold value may increase by some order of magnitude, resulting in undetected artifacts.

In addition, for the wedge power signal, regions of near zero power are often encountered in the scale range selected for the wedge. Thus, the threshold value, set as a multiple of preceding power values, may often be set at too low a value.

Figure 10A:
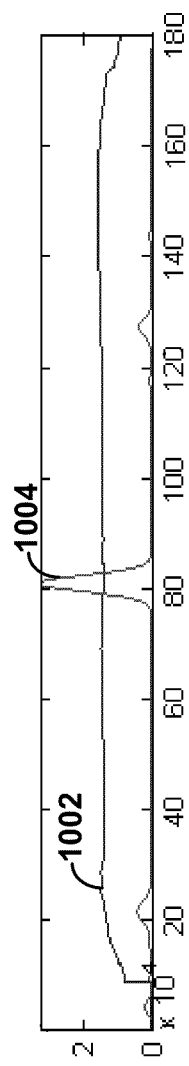
FIGS. 10(a), 10(b), and 10(c) show illustrative plots of a moving threshold adapting to an increase in the local minimum power due to movements in accordance with an embodiment.
Figure 10B:
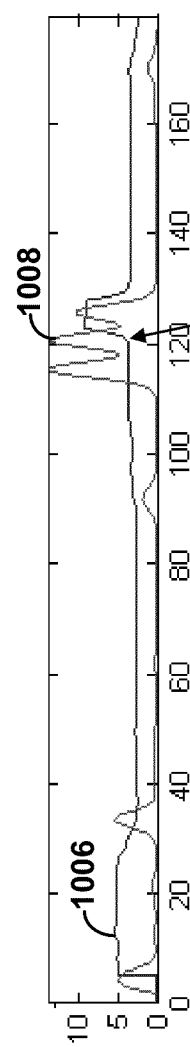
Figure 10C:
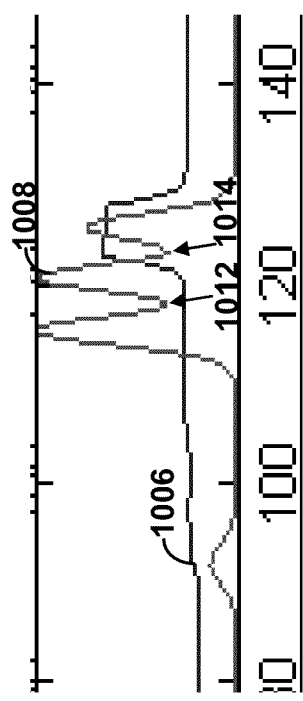
Figure 12A:
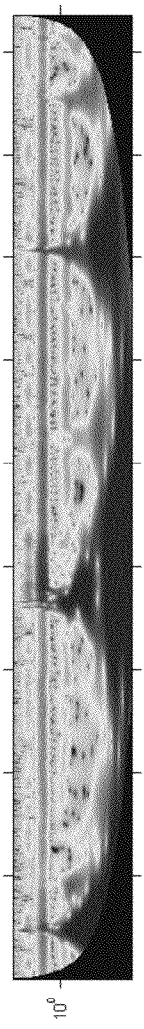
FIGS. 12(a), 12(b), 12(c), and 12(d) show illustrative movement artifact detector thresholds and an illustrative resulting masked scalogram in accordance with an embodiment.
Figure 12B:
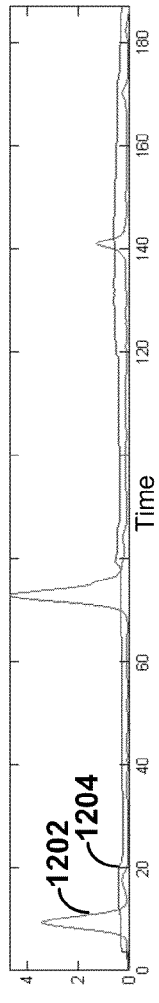
Figure 12C:
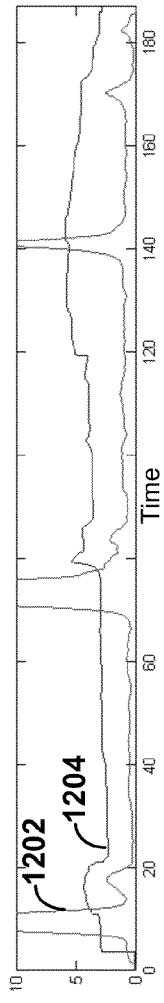
Figure 12D:
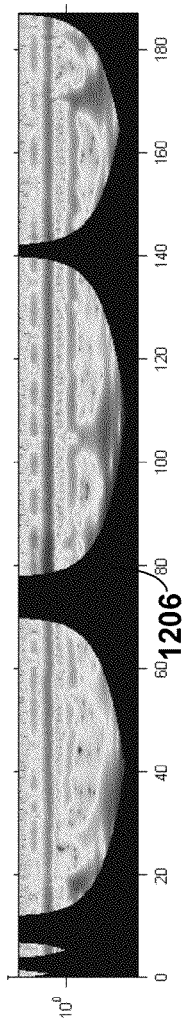

As such, in some embodiments, an improved threshold value may be computed by using the wedge power based on both a local and global component. The local component may be derived from the wedge power over a short window (e.g., 10 seconds), and the global component may be derived from a ridge power (e.g., the pulse ridge power) over a longer window (e.g., 60 seconds). In this way, the robust long-term threshold component may provide consistency along the signal, but in regions of multiple movement artifact, the local component may provide the relatively short, sharp increase in threshold required. This is generally illustrated in FIGS. 10(a), 10(b), and 10(c). These figures show plots of the moving threshold responding to one or more movement artifacts in a physiological signal (e.g., a PPG signal). For example, FIG. 10(a) shows single movement artifact 1004. As shown in FIG. 10(a), moving threshold 1002 is not affected by single movement artifact 1004; however, moving threshold 1006 may react to the increase in the local minimum power level caused by multiple consecutive movement artifacts 1008 as shown in FIG. 10(b). In FIG. 10(b), arrow 1010 indicates the start of the moving threshold 1006 increase due to an increase in local minimum power level caused by multiple movement artifacts 1008. FIG. 10(c) shows an enlarged version of the multiple consecutive movement artifact area of FIG. 10(b) for clarity. In FIG. 10(c), the local minimum power levels are indicated by arrows 1012 and 1014. Moving threshold 1006 decreases very soon after the artifact group dies away.

In some embodiments, low percentiles of the power signals are selected for use in the computation of the threshold components through, for example, trial and error. After selecting a suitable percentile, the power signal may then be scaled back up by multiplying the power signal by some multiple.

For example, in some embodiments, the 20th percentile of the global (pulse ridge) power may be selected. This selection may provide a reasonably stable representation of the ridge power, avoiding both regions of high excursion from the pulse ridge and less common dips in the pulse ridge due to artifact. The 5th percentile of the local (wedge energy) power may be selected in some embodiments. This selection may allow the local minima within artifact groupings to be characterized well. It may also provide for a reasonable length of time within the inspection window (e.g., 10 second inspection window) before the local threshold component has increased. Conversely, it may produce a reduction in the local threshold component very soon after the end of this artifact grouping due to the low percentile of the local energy used in setting the threshold value.

In an embodiment, after the moving threshold value is computed, it may be compared to one of the power measures described above (e.g., the moving wedge power measure). Areas where the power measure exceed the moving threshold value may then be identified as areas of movement, and a resultant scalogram mask may be created.

The same settings may be used for the adult and child signals, but, in some embodiments, different settings may be used for the neonatal signals. Illustrative algorithm settings according to an embodiment are shown in the table 1100 of FIG. 11. The settings which, in some embodiments, may differ for adult/child and neonatal signals are shown bold in the final two columns of the table. In other embodiments, other settings shown in table 1100 may differ for adult/child and neonatal signals, or, alternatively, the settings may be the same for both adult/child and neonatal signals.

In general, the values of the global threshold multiple may be markedly different for adult/child and neonatal use. This is because artifact energies in neonates may be typically much greater than the pulse ridge energies. Conversely, artifact energies in adults are typically less than the pulse ridge energies.

After the regions of movement are defined, a mask may be computed for the scalogram. The mask may be chosen to "mask" movement artifact from the scalogram. Masking movement artifact may include removing, replacing, ignoring, filtering, zeroing out, or otherwise modifying the areas of movement in the scalogram. For example, in some embodiments, areas of movement artifact are ignored in the computation of a parameter (e.g., a physiological parameter) derived from the scalogram. In other embodiments, the scalogram mask is used to actually create and/or store an enhanced scalogram. By filtering out the areas corresponding to movement artifacts only clean segments of the scalogram may be used in determining the parameter. Regions on one or both sides of the identified movement regions may also be masked in some embodiments. For example, side skirts (e.g., generally exponentially decaying side boundaries extending out on one or both sides an identified movement region) may also be added to the mask in some embodiments. The mask also may be used to identify regions of artifact. These regions may then be tagged for future reference, for example, for use in a signal quality measure or to identify regions which need further analysis. The mask may also be used to select a region of the scalogram that may be altered or modified. Such alterations or modifications can be used to produce an enhanced scalogram which is useful in suppressing the effects of artifact.

FIGS. 12(*a*), 12(*b*), 12(*c*), and 12(*d*) show an illustrative example of the movement artifact detection technique and the resulting masked scalogram. Although the detection method may be used to detect movement artifacts, the method may similarly be used to detect, remove, or filter other types of noise or noise artifacts.

FIG. 12(*a*) shows an illustrative original scalogram derived from a suitable physiological signal (e.g., a neonatal PPG), according to an embodiment. FIG. 12(*b*) is a plot of wedge power 1202 together with combined threshold 1204 derived from both a local and global wavelet component, according to an embodiment. An enlarged version of the plot shown in FIG. 12(*b*) is shown in FIG. 12(*c*) for clarity. Finally, FIG. 12(*d*) shows a plot of the resulting scalogram mask produced by the artifact detection techniques described above, according to an embodiment. As can be seen from FIG. 12(*d*), regions of increased artifact noise (e.g., regions corresponding to excessive movement) have been identified by mask 1206 and removed, filtered, or ignored from the scalogram or replaced. This enhanced scalogram may then be analyzed to determine more reliable and accurate physiological parameters.

As such, a method and system has been disclosed to detect regions of noise (e.g., movement artifact) in wavelet space. The detector may be based on a moving threshold value derived from a combination of the power represented by the wavelet ridge and the power within a predefined moving wedge region in wavelet space. A time-scale mask may then be created from the regions where a power measure (e.g., a moving wedge power measure) exceeds this moving threshold value.

Although the embodiments described herein generally relate to PPG signals, those skilled in the art will recognize that the present disclosure has wide applicability to other types of signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In some embodiments, a training phase may also be initiated where the parameters shown in table 1100 (FIG. 11) are first automatically varied to determine the optimal operating parameters for adult, child, and neonatal use. In the training phase, a series of known or reference physiological parameters may be used to determine the optimal artifact detection parameters. Default parameters may be varied on-the-fly by periodically executing the training phase during artifact detection.

In addition, in some embodiments, the artifact detection techniques described herein may also be incorporated within the ridge-based methods of respiration monitoring, where erroneous ridges due to movement artifact can be identified automatically and removed from the analysis in a similar manner as described above.

Figure 13:
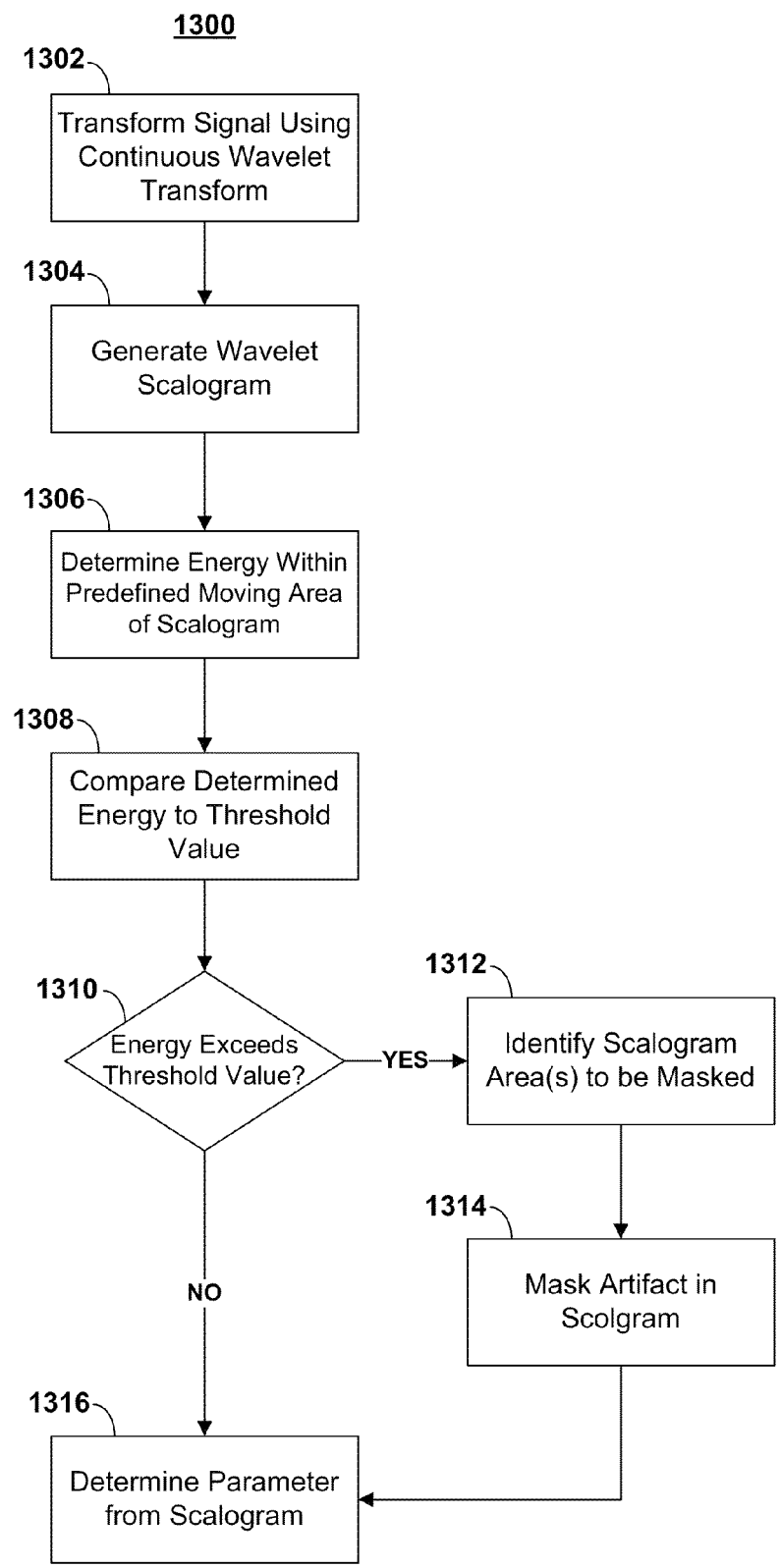
FIG. 13 shows an illustrative process for detecting artifacts in a signal in accordance with an embodiment.

FIG. 13 shows illustrative process 1300 for detecting artifacts in signals. At step 1302, a detected signal may be transformed using a wavelet transform (e.g., a continuous wavelet transform). For example, as described above, sensor 12 (FIG. 2) may detect a physiological signal (e.g., a PPG signal) from patient 40 (FIG. 2). Microprocessor 48 (FIG. 2) or processor 412 (FIG. 4) may then compute the wavelet transform of the detected signal. At step 1304, a wavelet scalogram may be generated. For example, in some embodiments, microprocessor 48 (FIG. 2) or processor 412 (FIG. 4) may apply equation

(10) to the continuous wavelet transform from step 1302 in order to produce a wavelet scalogram.

After the wavelet scalogram has been generated, at step 1306 the energy within one or more predefined moving areas of the wavelet scalogram may be determined. For example, in some embodiments, the energy within a generally wedge shaped moving area (e.g., wedge region 800 of FIG. 8) may be computed by microprocessor 48 (FIG. 2) or processor 412 (FIG. 4) using, for example, equation (21). Because some types of artifacts in a wavelet scalogram, including movement artifacts, may generally exhibit a generally wedge shaped artifact area, computing the energy within a wedge shaped area of the wavelet scalogram may enable more reliable artifact detection for some types of artifacts.

At step 1308, the energy determined at step 1306 may be compared to a threshold energy level. The threshold energy level may be based, for example, on previously detected energy measurements (e.g., a running or moving average of previously detected energy measurements), the energy of the pulse band, a predetermined threshold, and/or any combination thereof. As described above, in some embodiments, the threshold level may include both a local and global component. The local component may be derived from the wedge power over a short window, and the global component may be derived from the ridge power over a longer window.

At step 1310, microprocessor 48 (FIG. 2) or processor 412 (FIG. 4) may determine if the determined energy at step 1306 exceeds the threshold level. If the level is exceeded, at step 1312 one or more areas within the scalogram are identified for masking.

As described above, areas of the scalogram corresponding to movement may then be masked at step 1314 in some embodiments based, at least in part, on the areas of the scalogram identified in step 1312. As mentioned above, masking the artifact may include ignoring, filtering, zeroing, removing, replacing, or otherwise modifying the areas or segments of the scalogram corresponding to movement artifact. At step 1314, regions on one or both sides of the artifact area may also be masked. For example, generally exponentially decaying side skirts may be added on one or both boundaries of the movement areas (as shown in FIG. 12(*d*)). The mask also may be used to identify regions of artifact. These regions may then be tagged for future reference, for example, for use in a signal quality measure or to identify regions which need further analysis. The mask may also be used to select a region of the scalogram that may be altered or modified.

After the areas in the scalogram are ignored, filtered, replaced, or otherwise modified (or if the determined energy does not exceed the threshold energy level at step 1310), at step 1316 a parameter may be determined or derived from the enhanced scalogram or from the portion of the original scalogram that is not ignored. The enhanced scalogram may include less artifact noise (e.g., movement artifacts) as welt as other sources noise. Accordingly, from the enhanced scalogram, physiological parameters such as pulse rate, respiration rate, respiratory effort, and oxygen saturation, may all be detected more reliably.

In practice, one or more steps shown in process 1300 may be combined with other steps, performed in any suitable order, performed in parallel (e.g., simultaneously or substantially simultaneously), or removed.

The foregoing is merely illustrative of the principles of this disclosure and various modifications can be made by those skilled in the art without departing from the scope and spirit of the disclosure. The above described embodiments are presented for purposes of illustration and not of limitation. The present disclosure also can take many forms other than those explicitly described herein. Accordingly, it is emphasized that the disclosure is not limited to the explicitly disclosed methods, systems, and apparatuses, but is intended to include variations to and modifications thereof which are within the spirit of the following claims.

What is claimed is:

1. A method for detecting an artifact in a signal, the method comprising:
    transforming, using control circuitry, the signal using a continuous wavelet transform to generate a transformed signal;
    generating a wavelet scalogram based, at least in part, on the transformed signal;
    determining energy within a predefined moving area of the wavelet scalogram;
    comparing the determined energy within the predefined moving area of the wavelet scalogram to a threshold value; and
    masking at least one area of artifact in the wavelet scalogram based, at least in part, on the comparison.

2. The method of claim 1 wherein masking at least one area of artifact in the wavelet scalogram comprises filtering, ignoring, replacing, removing, zeroing out, and/or modifying a portion of the wavelet scalogram.

3. The method of claim 1 further comprising generating an enhanced wavelet scalogram based, at least in part, on the masking.

4. The method of claim 3 further comprising analyzing the enhanced wavelet scalogram to determine at least one physiological parameter.

5. The method of claim 4 wherein the physiological parameter comprises pulse rate, respiration rate, respiratory effort, and/or oxygen saturation.

6. The method of claim 1 wherein determining the energy within a predefined moving area of the wavelet scalogram comprises determining the energy within a moving wedge shaped area of the wavelet scalogram.

7. The method of claim 1 further comprising determining a pulse ridge energy of the wavelet scalogram, wherein the threshold value is based, at least in part, on the determined pulse ridge energy.

8. The method of claim 1 wherein the threshold value is based on at least a local wavelet component and a global wavelet component.

9. The method of claim 8 wherein the local wavelet component is derived from the energy within the predefined moving area of the wavelet scalogram over a first time window, and the global wavelet component is derived from a pulse ridge energy over a second time window, wherein the second time window is longer than the first time window.

10. The method of claim 1 wherein the threshold value is based, at least in part, on a running or moving average of the determined energy within the predefined moving area of the wavelet scalogram.

11. A system for detecting an artifact in a signal, the system comprising:
    a sensor capable of generating a signal; and
    a processor capable of:
        transforming the signal using a continuous wavelet transform to generate a transformed signal;
        generating a wavelet scalogram based, at least in part, on the transformed signal;
        determining energy within a predefined moving area of the wavelet scalogram;
        comparing the determined energy within the predefined moving area of the wavelet scalogram to a threshold value; and masking at least one area of artifact in the wavelet scalogram based, at least in part, on the comparison.

12. The system of claim 11 wherein the processor is capable of masking at least one area of artifact in the wavelet scalogram by filtering, ignoring, replacing, zeroing out, and/or modifying a portion of the wavelet scalogram.

13. The system of claim 11 wherein the processor is capable of generating an enhanced wavelet scalogram based, at least in part, on the masking.

14. The system of claim 13 wherein the processor is capable of analyzing the enhanced wavelet scalogram to determine at least one physiological parameter.

15. The system of claim 14 wherein the physiological parameter comprises pulse rate, respiration rate, respiratory effort, and/or oxygen saturation.

16. The system of claim 11 wherein the processor is capable of determining the energy within a moving wedge shaped area of the wavelet scalogram.

17. The system of claim 11 wherein the processor is capable of determining a pulse ridge energy of the wavelet scalogram, wherein the threshold value is based, at least in part, on the determined pulse ridge energy.

18. The system of claim 11 wherein the threshold value is based at least in part upon at least a local wavelet component and a global wavelet component.

19. The system of claim 18 wherein the local wavelet component is derived from the energy within the predefined moving area of the wavelet scalogram over a first time window, and the global wavelet component is derived from a pulse ridge energy over a second time window, wherein the second time window is longer than the first time window.

20. The system of claim 11 wherein the threshold value is based, at least in part, on a running or moving average of the determined energy within the predefined moving area of the wavelet scalogram.

21. A non-transitory computer-readable medium for use in detecting an artifact in a signal, the computer-readable medium having computer program instructions recorded thereon for:
    transforming the signal using a continuous wavelet transform to generate a transformed signal;
    generating a wavelet scalogram based, at least in part, on the transformed signal;
    determining energy within a predefined moving area of the wavelet scalogram;
    comparing the determined energy within the predefined moving area of the wavelet scalogram to a threshold value; and
    masking at least one area of artifact in the wavelet scalogram based, at least in part, on the comparison.

* * * * *